(12) United States Patent
Grot et al.

(10) Patent No.: US 7,151,597 B2
(45) Date of Patent: Dec. 19, 2006

(54) OPTICAL WAVELENGTH STANDARD AND OPTICAL WAVELENGTH CALIBRATION SYSTEM AND METHOD

(75) Inventors: Annette C. Grot, Cupertino, CA (US); Thomas J. Mikes, Wellington, FL (US)

(73) Assignee: Agilent Technologie, Inc, Sant Clara, CA (US)

( * ) Notice: Subject to any disclaimer, the term of this patent is extended or adjusted under 35 U.S.C. 154(b) by 401 days.

(21) Appl. No.: 10/729,508

(22) Filed: Dec. 5, 2003
(Under 37 CFR 1.47)

(65) Prior Publication Data

US 2005/0122512 A1    Jun. 9, 2005

(51) Int. Cl.
*G01J 1/10* (2006.01)
*G01N 21/55* (2006.01)

(52) U.S. Cl. .................................. 356/243.1; 356/445
(58) Field of Classification Search .. 356/243.1–234.8, 356/445
See application file for complete search history.

(56) References Cited

U.S. PATENT DOCUMENTS

| | | | |
|---|---|---|---|
| 4,664,522 A | 5/1987 | LeFebre | |
| 4,828,387 A * | 5/1989 | Sawyers et al. | 356/319 |
| 5,151,956 A | 9/1992 | Bloemer | |
| 5,268,737 A | 12/1993 | Fukuma et al. | |
| 5,303,028 A | 4/1994 | Milch | |
| 5,365,054 A | 11/1994 | Fathauer et al. | |
| 5,673,109 A | 9/1997 | Keilbach | |
| 5,986,808 A | 11/1999 | Wang | |
| 6,330,062 B1 | 12/2001 | Corn et al. | |
| 6,330,387 B1 | 12/2001 | Salamon et al. | |
| 6,340,448 B1 | 1/2002 | Naya et al. | |
| 6,377,899 B1 | 4/2002 | Sakai et al. | |
| 6,414,750 B1 | 7/2002 | Jung et al. | |
| 6,415,073 B1 | 7/2002 | Cappiello et al. | |
| 6,421,179 B1 | 7/2002 | Gutin et al. | |

(Continued)

FOREIGN PATENT DOCUMENTS

WO    WO 98/34098    8/1998

OTHER PUBLICATIONS

Dr. Paul dawson, "More Information on Surface Plasmons", http://www.qub.ac.uk/mp/con/plasmon/spl1.html, May 17, 1996.

(Continued)

*Primary Examiner*—Richard A. Rosenberger

(57) ABSTRACT

The optical wavelength standard comprises a diffraction grating having a diffractive surface, an input arrangement and an output optical arrangement. The input optical arrangement is located to illuminate the diffractive surface of the diffraction grating with incident light at an angle of incidence at which absorption of the incident light at a resonance wavelength generates surface plasmons. The output optical arrangement is located to receive the incident light specularly reflected from the diffractive surface of the diffraction grating as reflected light. The reflected light includes an absorption line at the resonance wavelength. The absorption line provides the wavelength reference. The resonance wavelength is defined by the angle of incidence and the physical characteristics of the diffraction grating. A desired resonance wavelength can be obtained by appropriately defining the angle of incidence and the physical characteristics of the diffraction grating. Moreover, the resonance wavelength can be changed by changing either or both of the angle of incidence and the diffraction grating.

24 Claims, 7 Drawing Sheets

U.S. PATENT DOCUMENTS

| | | |
|---|---|---|
| 6,430,341 B1 | 8/2002 | Russell et al. |
| 6,466,323 B1 | 10/2002 | Anderson et al. |
| 6,466,715 B1 | 10/2002 | Akiba et al. |
| 6,570,657 B1 * | 5/2003 | Hoppe et al. ............... 356/445 |
| 2003/0113231 A1 * | 6/2003 | Karube et al. ........... 422/82.05 |

OTHER PUBLICATIONS

IUPAC Manual, "Quantities, Units and Symbols in Physical Chemistry," 1988 (pub.for IUPAC by Blackwell Scientific Pulbications, Oxford 1988), pp. 22-28.

* cited by examiner

OPTICAL WAVELENGTH STANDARD AND OPTICAL WAVELENGTH CALIBRATION SYSTEM AND METHOD

BACKGROUND

Light subject to calibration is typically calibrated in wavelength by comparing its wavelength to an optical wavelength reference. Some types of optical wavelength references provide reference light in which an accurately-defined reference wavelength is marked. The reference wavelength is typically marked by a peak or a dip in the spectrum of the reference light at the reference wavelength. Based on such comparison, the optical calibration system determines the difference between the wavelength of the light subject to calibration and the reference wavelength in the reference light. To calibrate the wavelength of the light subject to calibration, the wavelength of the light subject to calibration is adjusted to match the reference wavelength in response to the wavelength difference.

Two common methods for generating the reference light are atomic emission and molecular absorption. In atomic emission, the reference light is generated by exciting atoms of a gas sealed in a hermetic chamber. Light emitted via excitation of the gas atoms has a particular wavelength, i.e., the reference wavelength, that depends on the type of gas contained in the chamber.

In molecular absorption, light having a range of wavelengths, e.g., white light, broad-band ultra-violet light, etc., is passed through a gas sealed in a hermetic chamber. The gas molecules absorb light from the light passing through the chamber at one or more wavelengths that depend on the type of gas contained in the chamber. Thus, the spectrum of the light after passing through the chamber has an absorption line at each of the one or more wavelengths. One of these wavelengths is designated as the reference wavelength.

Generating reference light using either atomic emission or molecular absorption employs a device having a hermetic chamber containing a particular gas for marking the reference wavelength. Such a device, sometimes referred to as a "gas lamp," is typically expensive. Moreover, the reference light generated by such a device has relatively few reference wavelengths. Additionally, the reference wavelengths depend on the type of gas contained in the hermetic chamber. The reference wavelengths available may not be conveniently close in wavelength to the desired calibration wavelength. Moreover, the reference wavelengths cannot easily be changed.

Thus, an unaddressed need exists for an optical wavelength standard that is lower in cost than a conventional optical wavelength standard and that and is capable of providing a greater number of reference wavelengths in a given wavelength range than a conventional optical wavelength standard.

SUMMARY OF THE INVENTION

In a first aspect, the invention provides an optical wavelength standard that comprises a diffraction grating having a diffractive surface, an input arrangement and an output optical arrangement. The input optical arrangement is located to illuminate the diffractive surface of the diffraction grating with incident light at an angle of incidence at which absorption of the incident light at a resonance wavelength generates surface plasmons. The output optical arrangement is located to receive the incident light specularly reflected from the diffractive surface of the diffraction grating as reflected light. The reflected light includes an absorption line at the resonance wavelength. The absorption line provides the wavelength reference.

In a second aspect, the invention provides an optical wavelength calibration system for calibrating the wavelength of light subject to calibration generated by a light source subject to calibration at a wavelength determined by a control signal. In a first embodiment, the optical calibration system comprises the above-described optical wavelength standard in accordance with the invention, an auxiliary light source and an optical calibration apparatus. The auxiliary light source is operable to generate the incident light in a wavelength range that spans the resonance wavelength. In the optical wavelength standard, the input optical arrangement is arranged to receive the incident light from the auxiliary light source. The optical calibration apparatus is arranged to receive the light subject to calibration and additionally to receive the reflected light from the output optical arrangement. The optical calibration apparatus is operable to perform a wavelength comparison between the absorption line in the reflected light and the light subject to calibration and to provide the control signal to the light source subject to calibration. The control signal represents a wavelength difference between absorption line and the light subject to calibration.

A second embodiment of the optical calibration system comprises the above-described optical wavelength standard in accordance with the invention and an optical calibration apparatus. In the optical wavelength standard, the input optical arrangement is arranged to receive the light subject to calibration from the light source subject to calibration as the incident light. The optical calibration apparatus is arranged to receive the reflected light from the output optical arrangement and is operable to generate the control signal in response to the intensity of the reflected light and to provide the control signal to the light source subject to calibration.

In a third aspect, the invention provides an optical wavelength calibration method. In the method, a diffraction grating comprising a diffractive surface is provided. Incident light is specularly reflected off the diffractive surface of the diffraction grating light at an angle at which absorption of the incident light at a resonance wavelength generates surface plasmons. The light reflected by the diffractive surface is received as reflected light. The reflected light has an absorption line at the resonance wavelength. The wavelength of the light subject to calibration is then calibrated using the absorption line in the reflected light as a wavelength reference.

In the optical wavelength standard, the optical wavelength calibration system and the optical wavelength calibration method in accordance with the invention, the resonance wavelength is defined by the angle of incidence and the physical characteristics of the diffraction grating. Hence, a desired resonance wavelength can be obtained simply by appropriately defining the angle of incidence and the physical characteristics of the diffraction grating. Moreover, the resonance wavelength can be changed simply by changing either or both of the angle of incidence and the diffraction grating.

BRIEF DESCRIPTION OF THE DRAWINGS

The invention can be better understood with reference to the following drawings. The elements of the drawings are not necessarily to scale relative to each other, emphasis instead being placed upon clearly illustrating the principles of the invention. Furthermore, like reference numerals designate corresponding parts throughout the several views.

DETAILED DESCRIPTION

Embodiments of the invention provide an optical wavelength standard, an optical wavelength calibration system that incorporates such optical wavelength standard and an optical wavelength calibration method. The optical wavelength standard, the optical wavelength calibration system and the optical wavelength calibration method use the absorption line created when incident light is specularly reflected by the diffractive surface of a diffraction grating as a reference wavelength. The diffraction grating is illuminated by incident light. The diffraction grating specularly reflects a portion of the incident light, i.e., the so-called zero order reflection. Illuminating any metallic surface causes surface plasma oscillations, which will be called surface plasmons, in the electron gas of the metal. The surface plasmons absorb part of the incident light. Structuring the metallic surface as the diffractive surface of a diffraction grating causes the light absorption to occur at a resonance wavelength that depends on the angle of incidence and the physical characteristics of the diffraction grating. Thus, the resonance wavelength is defined by the angle of incidence and the physical characteristics of the diffraction grating. Hence, a desired resonance wavelength can be obtained simply by appropriately defining the angle of incidence and the physical characteristics of the diffraction grating. Moreover, the resonance wavelength can be changed simply by changing either or both of the angle of incidence and the diffraction grating.

In a first embodiment, the diffractive surface of the diffraction grating is illuminated with incident light having a range of wavelengths that spans the resonance wavelength. The surface plasmons resonantly absorb the incident light at the resonance wavelength. Consequently, the portion of the incident light that is specularly reflected by the diffraction grating as reflected light has a spectrum that exhibits an absorption line at the resonance wavelength. The reflected light with the absorption line at the resonance wavelength is suitable for use as reference light in which the absorption line identifies the reference wavelength. The reference light can be used by a comparison-type optical wavelength calibration system to calibrate the wavelength of light subject to calibration to a calibration wavelength at or near the reference wavelength.

In a second embodiment, the diffractive surface of the diffraction grating is illuminated with the light subject to calibration as the incident light. The surface plasmons resonantly absorb the light subject to calibration when the wavelength of the light subject to calibration is equal to the resonance wavelength. Consequently, the intensity of the reflected light exhibits a minimum when the wavelength of the light subject to calibration is equal to the resonance wavelength.

Figure 1:
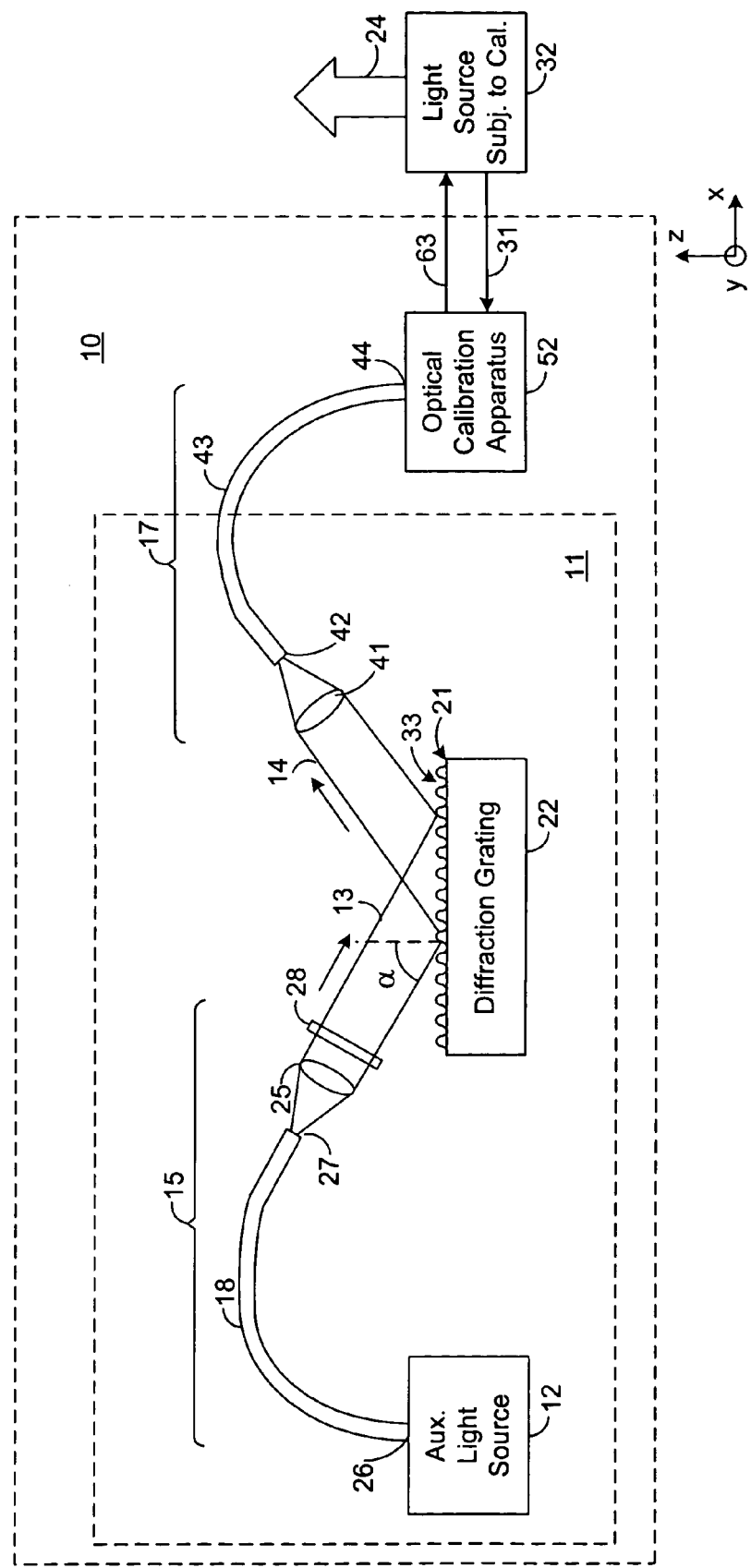
FIG. 1 is a block diagram illustrating a first exemplary embodiment of an optical wavelength calibration system in accordance with the invention. The optical wavelength calibration system incorporates a first embodiment of an optical wavelength reference in accordance with the invention.

FIG. 1 depicts an exemplary embodiment of an optical calibration system 10 in accordance with the invention. The optical calibration system incorporates a first embodiment 11 of an optical wavelength reference in accordance with the invention. The optical calibration system 10 is shown in use to calibrate the wavelength of light subject to calibration generated by a light source subject to calibration 32. The optical wavelength reference 11 is composed of an auxiliary light source 12, a diffraction grating 22, an input optical arrangement 15 and an output optical arrangement 17. The diffraction grating has a diffractive surface 21.

The input optical arrangement 15 is arranged to illuminate the diffractive surface 21 of diffraction grating 22 with polarized incident light 13 at a defined angle of incidence $\alpha$. In this embodiment, the input optical arrangement illuminates the diffractive surface with light received from the auxiliary light source 12 as the incident light 13.

The diffractive surface 21 of the diffraction grating 22 specularly reflects the incident light 13 as reflected light 14. The output optical arrangement 17 selects the reflected light from the light diffracted by the diffraction grating 22 and outputs the reflected light as reference light.

The optical calibration system 10 is composed of the optical wavelength standard 11 and the optical calibration apparatus 52. The optical calibration apparatus 52 is connected to the output optical arrangement 17 to receive the reference light generated by the optical wavelength standard 11. The optical calibration apparatus is additionally connected to receive sample light 31 from light source subject to calibration 32, which is not part of the optical calibration system. The sample light is a sample of the light subject to calibration 24 generated by the light source subject to calibration 32. Thus, the optical calibration apparatus can be said to receive the light subject to calibration. The optical calibration apparatus 52 is shown as providing a wavelength control signal 63 to the light source subject to calibration 32 to set the wavelength of the light subject to calibration to a desired wavelength defined by the optical wavelength standard 11. In the light source subject to calibration, the wavelength of the light subject to calibration is determined directly or indirectly by the control signal 63.

Figure 2:
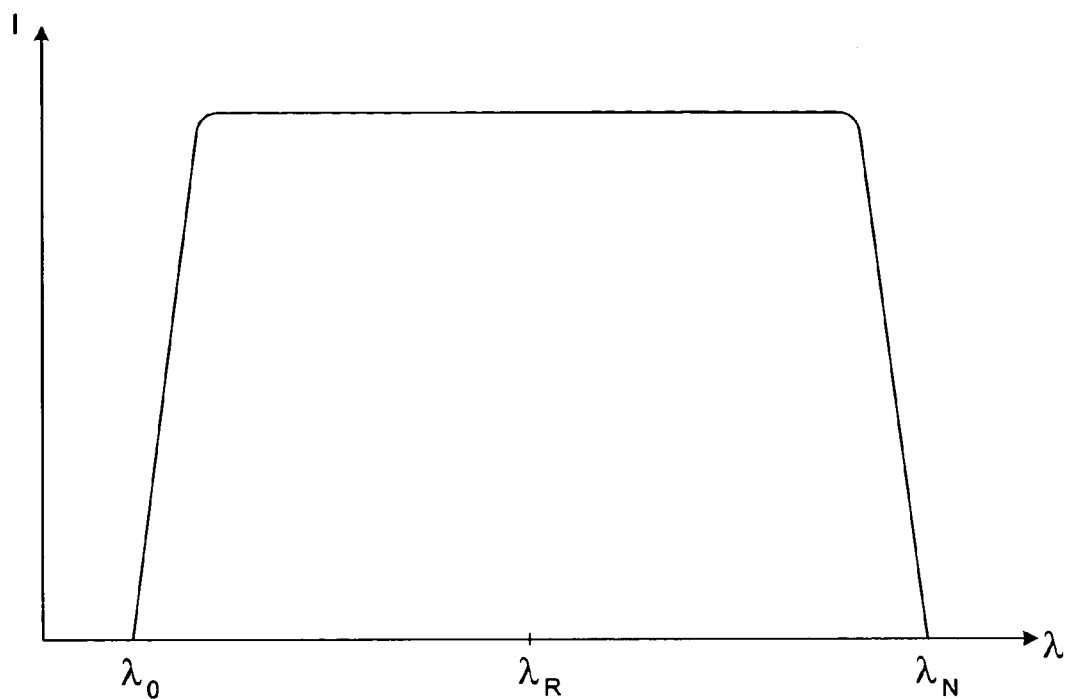
FIG. 2 is a graph illustrating the spectrum of the incident light that illuminates the diffractive surface of the diffraction grating in the embodiment of the optical wavelength reference depicted in FIG. 1.

The auxiliary light source 12 generates light having a range of wavelengths that spans the resonance wavelength of the diffraction grating 22. FIG. 2 shows an example of the spectrum of the light generated by the auxiliary light source 12. The spectrum shown in FIG. 2 is also the spectrum of the incident light 13. The wavelength range of the incident light extends from a lower wavelength $\lambda_0$ to an upper wavelength $\lambda_N$.

Referring again to FIG. 1, in the example shown, the input optical arrangement 17 is composed of an optical fiber 18, a collimator 25 and a polarizer 28. One end 26 of the optical fiber 18 is arranged to receive light from the auxiliary light source 12. The other end 27 of the optical fiber 18 is arranged to direct the incident light 13 towards the diffractive surface 21 of the diffraction grating 22. The collimator 25 and the polarizer are disposed in series between the end 27 of the optical fiber 18 and the diffractive surface 21.

The collimator 25 and the polarizer 28 respectively collimate and polarize the incident light 13 output by the optical fiber 18. In the example shown in FIG. 1, the collimator 25 is shown schematically as a convex lens. Other collimators capable of collimating light having a range of wavelengths are known in the art and may be used instead. The polarizer is arranged to orient the TM component of the incident light 13 in the y-direction. The order of the collimator and the polarizer may be reversed from that shown.

In the example shown, the output optical arrangement 17 that selects the reflected light 14 specularly reflected by the diffractive surface 21 of the diffraction grating 22 and outputs the reflected light as reference light is composed of a focusing element 41 and an optical fiber 43. One end 42 of the optical fiber 43 is arranged to receive the reflected light 14 specularly reflected by the diffractive surface 21. The focusing element 41 focuses the reflected light 14 on the end 42 of the optical fiber 43. The reflected light 14 is output from the end 44 of the optical fiber 43 as reference light. In the example shown, the end 44 of the optical fiber 43 is shown connected to deliver the reference light to the optical calibration apparatus 52. The focusing element 41 is interposed between the end 42 of the optical fiber 43 and the diffractive surface 21. The focusing element 41 focuses the reflected light 14 on the end 42 of the optical fiber 43. In the example shown in FIG. 1, the focusing element 41 is shown schematically as a convex lens. Other focusing elements capable of focusing light having a range of wavelengths are known in the art and may be used instead.

The angle of incidence a of the incident light on diffractive surface 21 is such that the resonance wavelength of the surface plasmons at the diffractive surface 21 of the diffraction grating 22 is at the desired reference wavelength of the optical wavelength standard 11. Moreover, the profile of the grooves 33 of the diffractive surface is optimized as is known in the art to maximize specular reflection of the incident light 13 by the diffractive surface 21. The resonance wavelength in the wavelength range $\lambda_0$–$\lambda_N$ of the incident light 13. As a result, the surface plasmons at the diffractive surface 21 absorb a significant fraction of the intensity of the incident light at the resonance wavelength. The diffractive surface 21 specularly reflects the remainder of the wavelength range of the incident light as reflected light 14.

Figure 3:
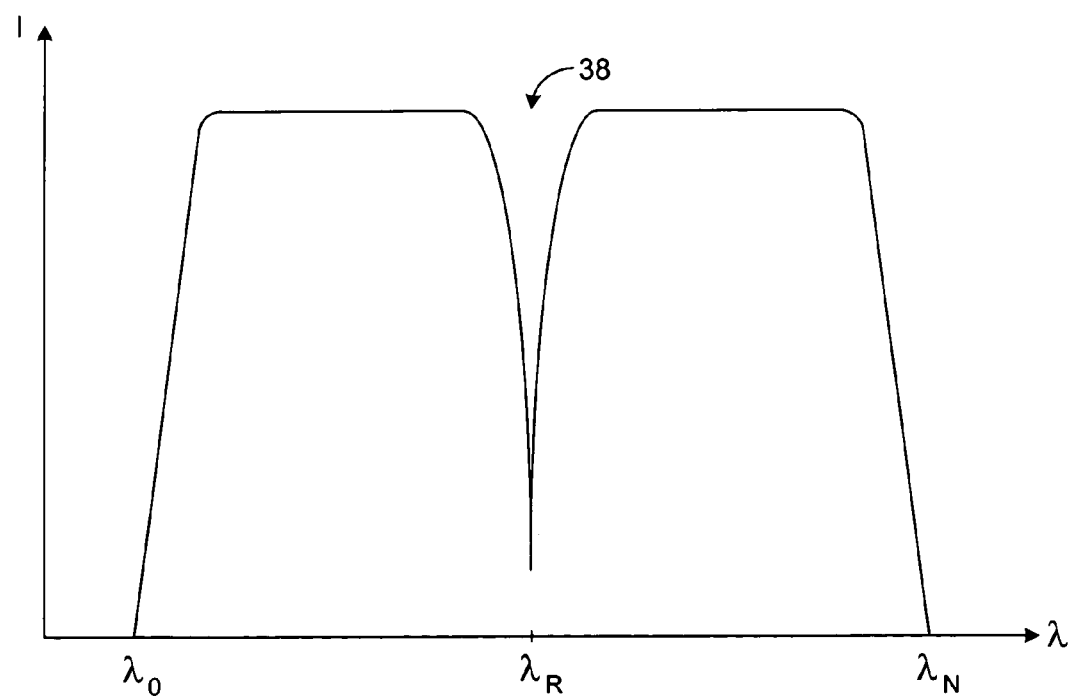
FIG. 3 is a graph illustrating the spectrum of the reflected light reflected by the diffractive surface of the diffraction grating in the embodiment of the optical wavelength reference depicted in FIG. 1.

FIG. 3 shows the spectrum of the reflected light 14. The spectrum of the reflected light exhibits an absorption line 38 at the reference wavelength $\lambda_R$, which is equal to the resonance wavelength of the surface plasmons at the diffractive surface 21. The reflected light 14 is output as reference light in which the absorption line provides the reference wavelength $\lambda_R$. The optical calibration system 10 uses the reference light to calibrate the wavelength of the light subject to calibration, as will be described in more detail below.

The reference wavelength $\lambda_R$ is equal to or near the desired wavelength to which the light subject to calibration generated by the light source subject to calibration 32 is to be calibrated. For example, if it is desired to calibrate the light source 32 using a reference wavelength of 1600 nanometers (nm), then the diffractive surface 21 of diffraction grating 22 and the angle of incidence ζ are configured to set the reference wavelength $\lambda_R$ to 1600 nm. As a result, the reflected light 14 reflected by the diffractive surface 21 has an absorption line at 1600 nm. The calibration system 10 uses the absorption line in the reflected light 14 as a wavelength marker for calibrating the light source 32. In other examples, the surface plasmons of the diffractive surface 21 resonate at frequencies corresponding to other wavelengths of the incident light 13 to provide reflected light having absorption lines that mark other desired wavelengths.

Figure 4:
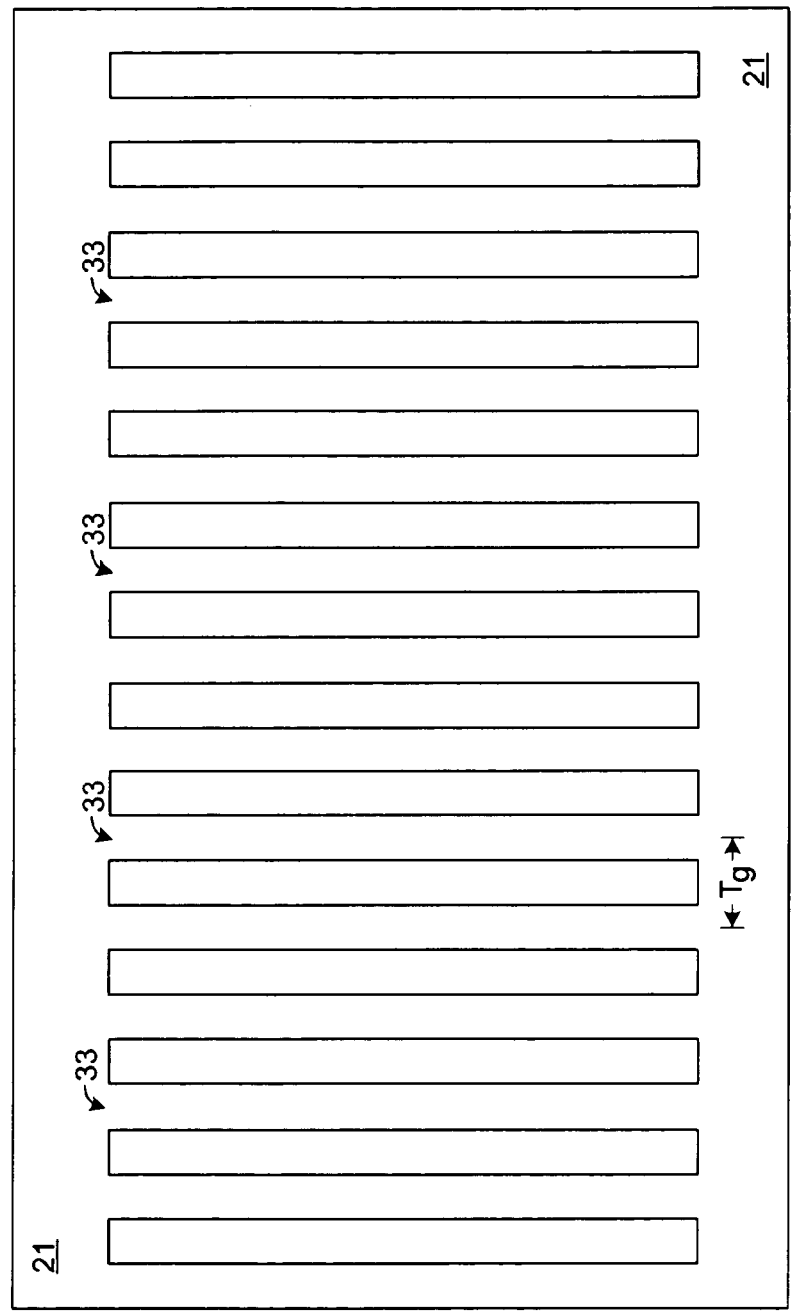
FIG. 4 is a top view of an example of the diffraction grating depicted in FIG. 1.

The diffractive surface 21 of the diffraction grating 22 is configured to absorb light at a desired reference wavelength. In one embodiment, the diffraction grating 22 has grooves 33 extending across its diffractive surface 21, as shown in FIGS. 1 and 4. The grooves 33 are substantially parallel to one another and are disposed in a direction parallel to the plane of the incident light. The grooves are also of uniform shape to better control the optical frequency at which the surface plasmons resonate, as will be further described below.

The distance between centers of adjacent grooves 33, i.e., the pitch $T_g$ of the grooves 33 is the same for all grooves 33 such that the grooves 33 appear periodic in the x-direction. The x-direction is orthogonal to the y-direction, which is the direction in which the grooves 33 extend, as shown in FIGS. 1 and 4.

The optical frequency at which the surface plasmons of the diffractive surface 21 resonate and, therefore, the reference wavelength $\lambda_R$ depend on various factors, including the groove pitch $T_g$ of the diffractive surface 21 and the angle of incidence α of the incident light 13 on the diffractive surface 21.

Techniques for constructing and using a diffraction grating such that surface plasmons of the grating resonate at an optical frequency corresponding to a particular wavelength of incident light are known in the art. In particular, for the surface plasmons of a diffraction grating to resonate in response to incident light of reference wavelength $\lambda_R$, the component of the incident light wave vector in the x-direction should match the component in the x-direction of the wave vector of the electromagnetic field due to the surface plasmons at diffractive surface 21. This condition may be expressed as:

$$\vec{k}_x = \vec{k}_g + \vec{k}_0 \cdot \sin \alpha$$

where $\vec{k}_x$ represents the component in the x-direction of the wave vector of the electromagnetic field due to the surface plasmons, $\vec{k}_0$ is the wave vector of the incident light, $\vec{k}_g$ is the wave vector of diffractive surface 21 and α is the angle of incidence of incident light 13 relative to the normal to the diffractive surface. The component $\vec{k}_x$ in the x-direction of the electromagnetic field due to the surface plasmons and is given by:

$$\vec{k}_x = \vec{k}_0 \sqrt{\frac{\varepsilon_0 \varepsilon_g}{\varepsilon_0 + \varepsilon_g}}$$

where $\epsilon_0$ is the dielectric constant of air, $\epsilon_g$ is the dielectric constant of the material of diffractive surface 21, and depends on the reference wavelength, and $\vec{k}_0$ is equal to $2\pi/\lambda_R$. The wave vector $\vec{k}_g$ of diffractive surface 21 is equal to $2\pi/T_g$, where $T_g$ is the groove pitch of the diffractive surface.

To determine the angle of incidence α that produces a surface plasmons resonance at reference wavelength $\lambda_R$ using diffractive surface 21 with a groove pitch $T_g$ and of a material with a dielectric constant $\epsilon_m$, the above equations are rearranged to give:

$$\alpha = \sin^{-1}\left\{\sqrt{\frac{\epsilon_0 \epsilon_g}{\epsilon_0 + \epsilon_g}} - \frac{\lambda}{T_g}\right\}$$

To enhance the absorption by the surface plasmons of the incident light at the reference wavelength $\lambda_R$, the material of at least the diffractive surface 21 of the diffraction grating 22 is conductive. In one example, the material of the conductive surface 21 is gold (Au). Furthermore, to reduce drift from changes in temperature, diffractive surface 21 of the grating 22 is located on a substrate of a material having a low or zero coefficient of thermal expansion. Suitable materials include ZERODUR® glass, sold by Schott Corp., Yonkers, N.Y., and an alloy of iron, nickel and carbon sold under the trademark INVAR®. The temperature of the substrate may also be controlled to further reduce the temperature dependence of the resonant wavelength.

Referring again to FIG. 1, the optical calibration apparatus 52 receives the reference light from the optical fiber 43 and additionally receives the sample light 31 from the light source 32. The optical calibration apparatus 52 compares the reference wavelength $\lambda_R$ of the absorption line 38 in the reference light and the wavelength of the sample light and calibrates the light source 32 in response to the result of the comparison. The optical calibration apparatus 52 determines the difference between the wavelength of the sample light 31 and the reference wavelength $\lambda_R$ of the absorption line in the reference light. The optical calibration apparatus 52 feeds to the light source subject to calibration 32 the control signal 63 indicative of the determined wavelength difference. In response to the feedback signal 63, the light source 32 adjusts the wavelength of the light subject to calibration, and, hence, the wavelength of sample light 31, to a desired wavelength.

Figure 5A:
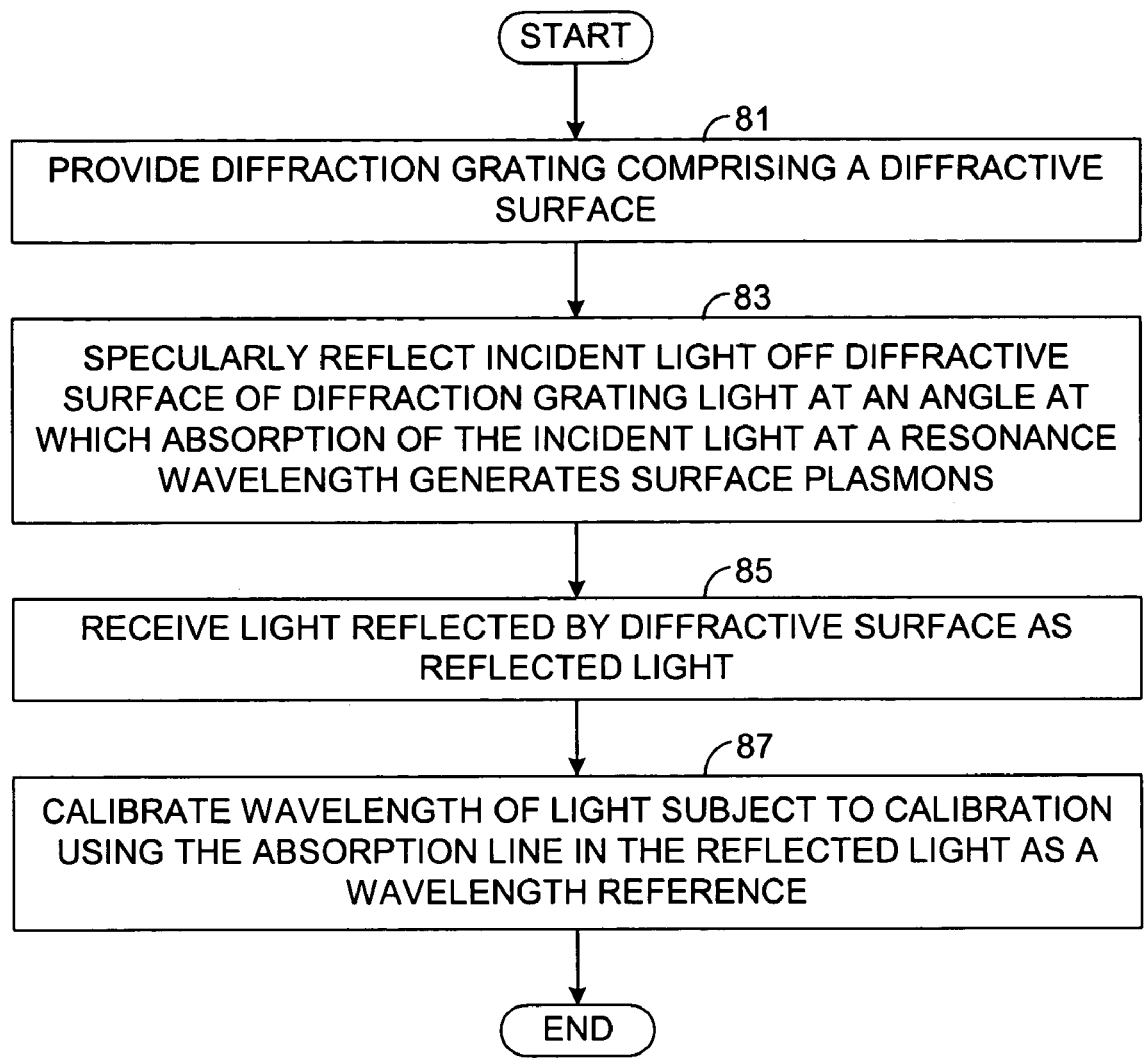
FIG. 5A is a flow chart illustrating an exemplary embodiment of an optical calibration method in accordance with the invention.

FIG. 5A is a flow chart that illustrates an embodiment of an optical wavelength calibration method in accordance with the invention. In block 81, a diffraction grating having a diffractive surface is provided. In block 83, incident light is specularly reflected off the diffractive surface of the diffraction grating light at an angle at which absorption of the incident light at a resonance wavelength generates surface plasmons In block 87, light reflected by diffractive surface as reflected light. The absorption of the incident light by the surface plasmons causes the spectrum of the reflected light to exhibit an absorption line at the resonance wavelength. The absorption line in the spectrum of the reflected light marks a reference wavelength. In block 89, the wavelength of light subject to calibration is calibrated using the absorption line in the reflected light as a wavelength reference.

Figure 5B:
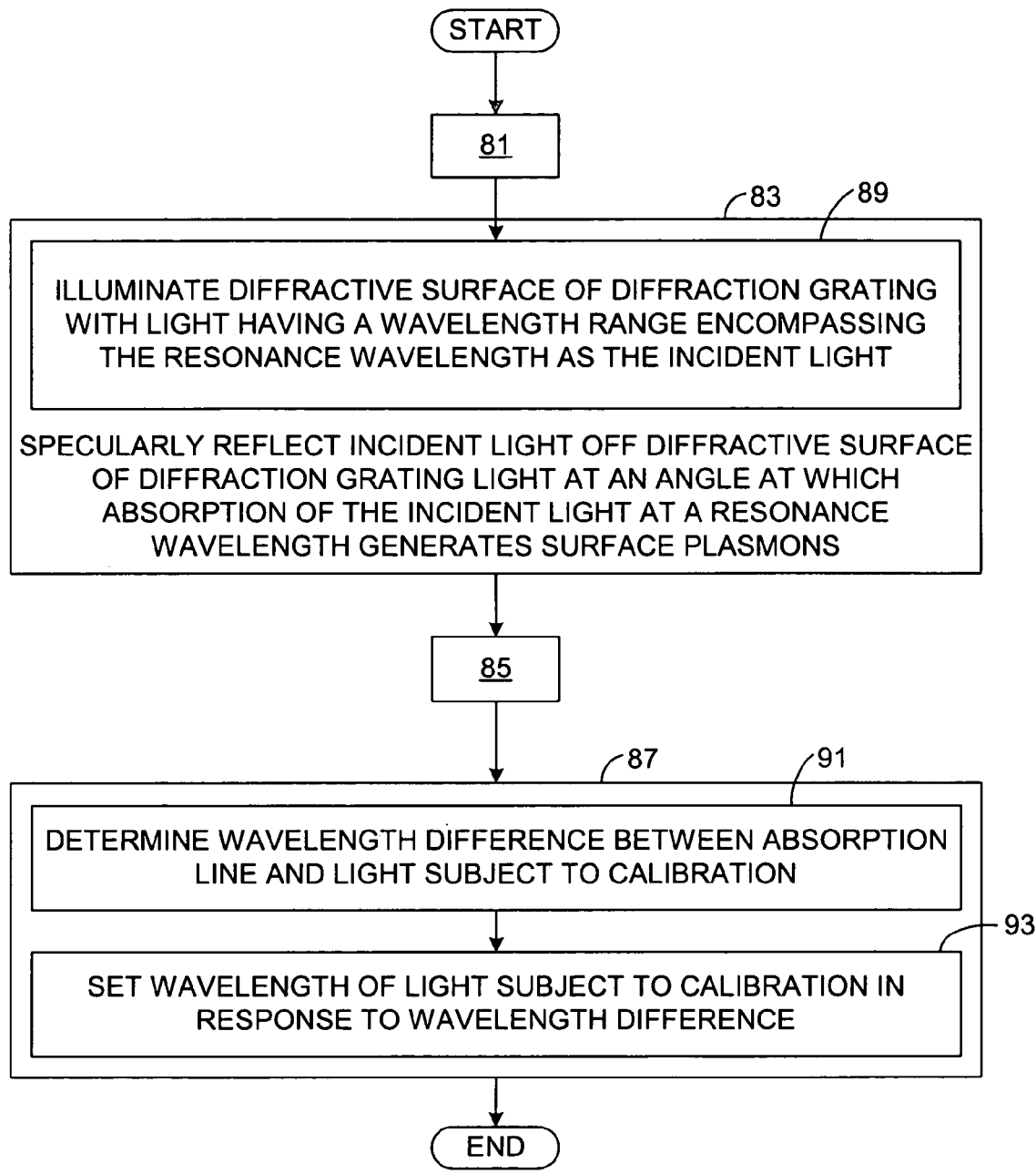
FIG. 5B is a flow chart that illustrates an example of the optical wavelength calibration method shown in FIG. 5A in which the incident light that illuminates the diffractive surface has a wavelength range that spans the resonance wavelength.

FIG. 5B is a flow chart that illustrates an example of the optical wavelength calibration method shown in FIG. 5A in which the incident light that illuminates the diffractive surface has a wavelength range that spans the resonance wavelength. Elements of the method shown in FIG. 5B that correspond to elements of the method shown in FIG. 5A are indicated using the same reference numerals and will not be described again.

The embodiment of block 83 shown in FIG. 5B includes block 89 in which the diffractive surface of the diffraction grating is illuminated with light having a wavelength range that spans the resonance wavelength as the incident light.

Block 87 in FIG. 5B is composed of blocks 91 and 93. In block 91, the wavelength difference between the absorption line in the reflected light and the light subject to calibration is determined. In block 93, the wavelength of the light subject to calibration is set in response to the wavelength difference.

In one example of the method just described, the light subject to calibration is to be calibrated to a wavelength of 1600 nm, the actual wavelength of the light subject to calibration is 1610 nm, and the wavelength of the absorption line in the reflected light is 1600 nm. In block 91, the wavelength of the light subject to calibration is compared with the wavelength of the absorption line in the reflected light and the difference between the wavelengths is determined to be 10 nm. In response to such a determination, in block 93, the wavelength of the light subject to calibration is set to 1600 nm in response to the wavelength difference. For example, a control signal is generated in block 93 indicating the amount by which the wavelength of the light subject to calibration should be adjusted to set the wavelength of the light subject to calibration to the wavelength of the absorption line in the reflected light.

In example of the method shown in FIG. 5B performed by the apparatus 10 shown in FIG. 1, the optical calibration apparatus 52 transmits a control signal 63 indicating that the wavelength of the light subject to calibration differs from the wavelength of the absorption line in the reflected light by 10 nm. In response to the feedback signal, the light source 32 reduces the wavelength of the light subject to calibration until the control signal indicates that the wavelength difference is zero. In response to the control signal, the light source 32 reduces the wavelength of the light subject to calibration by 10 nm to set the wavelength of sample light 31 to the desired wavelength, i.e., 1600 nm. The control signal may be an open-loop control signal or a closed-loop control signal.

It is not necessary to change the diffraction grating 22 or the angle of incidence in the event that the desired wavelength of the light subject to calibration is changed. For example, if the desired wavelength of the light subject to calibration is changed from 1600 nm, as described above, to 1605 nm, then the optical calibration apparatus 52 can be operated to calibrate the light source 32 to an output wavelength of 1605 nm instead of 1600 nm. After comparing the wavelength of the absorption line at 1600 nm in the reflected light 14 with the wavelength of the sample light 31 at 1610 nm, the optical calibration apparatus 52 outputs the control signal 63 indicating that the wavelength of the light subject to calibration differs from the reference wavelength by 10 nm. In response to the control signal, the light source 32 changes the wavelength of the light subject to calibration until the control signal indicates that the wavelength difference is equal to 5 nm. The light source 32 reduces the wavelength of the light subject to calibration by 5 nm to set the wavelength of sample light 31 to the desired wavelength, i.e., 1605 nm, which differs from the reference wavelength by 5 nm.

In an alternative embodiment, the reference wavelength is changed in the event that the desired wavelength of the light subject to calibration is changed. This allows the optical calibration apparatus to operate by setting the wavelength of the light subject to calibration to be equal to the reference wavelength indicated by the absorption line in the reflected light 14. For example, if the desired wavelength of the light subject to calibration is changed from 1600 nm to 1605 nm, as described above, rather than changing the configuration of the optical calibration apparatus 52, the reference wavelength of the reflected light 14 is changed from 1600 nm to 1605 nm. In this case, the optical calibration apparatus causes the light source 32 to reduce its wavelength until the wavelength of the sample light 31 is equal to the reference wavelength indicated by the absorption line in the reflected light 14.

The reference wavelength of the reflected light 14 can be changed by replacing the diffraction grating 22 with another diffraction grating structured such that the surface plasmons absorb light at a different wavelength from those of diffraction grating 22. In one example, the diffraction grating 22 is replaced by another diffraction grating having a pitch different from that of the diffraction grating 22. In another example, the diffraction grating 22 is replaced by a diffraction grating having the same pitch as the diffraction grating 22 but having a diffractive surface 21 of a different material. At the angle of incidence a, the surface plasmons in the replacement diffraction grating absorb the incident light at a different resonant wavelength from those of the diffraction grating 22, e.g., the surface plasmons of the replacement diffraction grating absorb the incident light at a wavelength of 1605 nm instead of 1600 nm.

Alternatively, the diffraction grating 22 may be retained and another parameter, such as the angle of incidence α, is altered to change the wavelength (e.g., to 1605 nm) of the reference wavelength defined by the absorption line in the reflected light 14. In an embodiment, a number of input optical arrangements each similar to the input optical arrangement 15 (FIG. 1) and each composed of an optical fiber similar to the optical fiber 18, a collimator similar to the collimator 25 and a polarizer similar to the polarizer 28 are arranged to illuminate the diffractive surface 21 of the diffraction grating 22 at different angles of incidence. The optical fibers are arranged so that a selected one of them receives light from the auxiliary light source 12 to define the angle of incidence of the incident light 13. Additionally, a corresponding number of output optical assemblies each similar to the output optical assembly 17 and composed of a focusing element similar to the focusing element 41 and an optical fiber similar to the optical fiber 43 are arranged to receive the reflected light specularly reflected by the diffraction grating 22. The optical fibers are arranged so that the one of them that receives the reflected light 14 is connected to the optical calibration apparatus 52.

In such alternative embodiments, the reflected light 14 exhibits an absorption line at a reference wavelength that matches the new desired wavelength of the light subject to calibration, and the optical calibration apparatus 52 simply calibrates the wavelength of the light subject to calibration generated by the light source 32 to match the reference wavelength of the absorption line in the reflected light 14, as described above.

Figure 6:
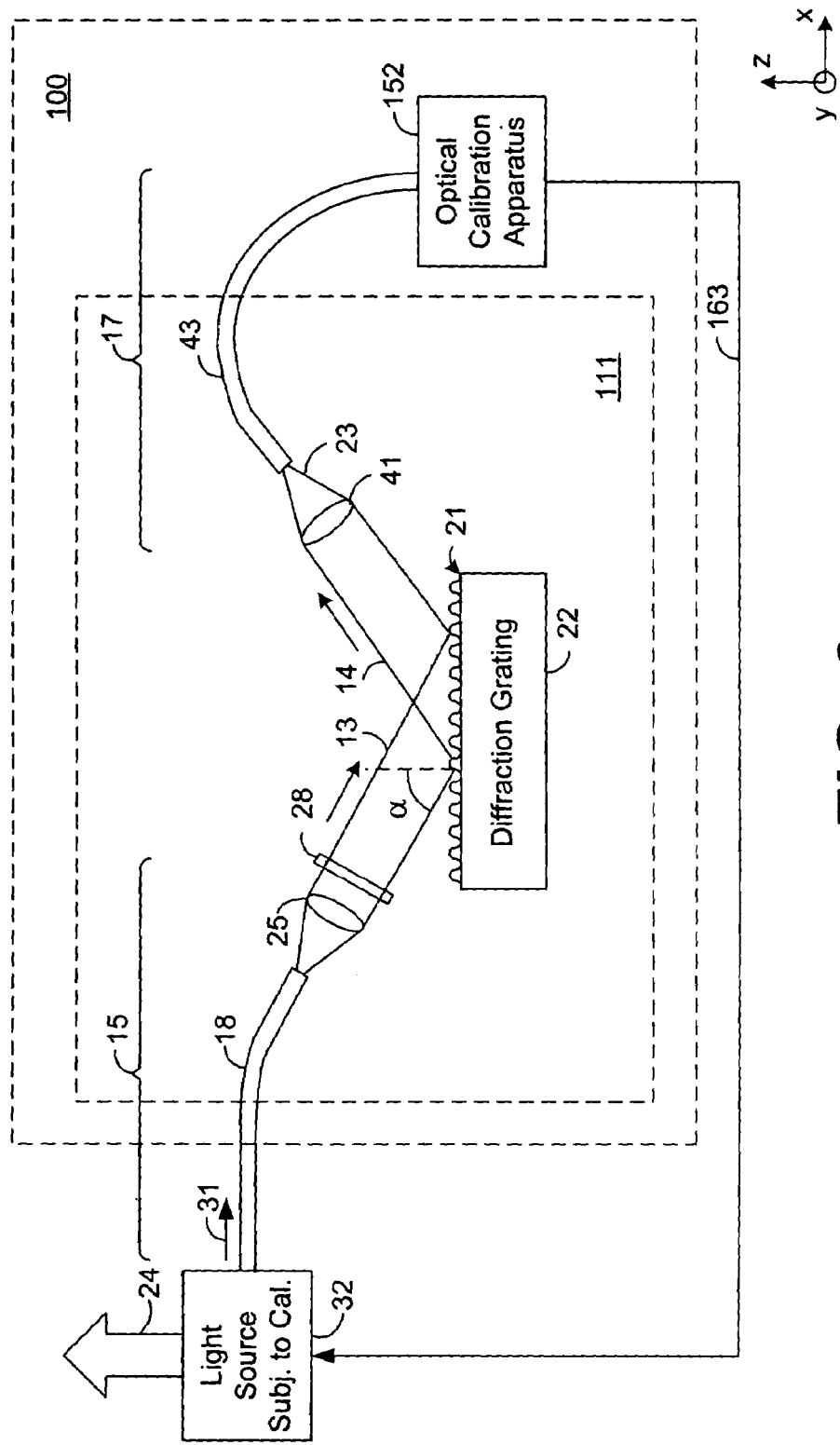
FIG. 6 is a block diagram illustrating a second exemplary embodiment of an optical calibration system in accordance with the invention. The optical wavelength calibration system incorporates a second embodiment of an optical wavelength reference in accordance with the invention.

FIG. 6 depicts another embodiment of an optical calibration system 100 in accordance with the invention. The optical calibration system is for calibrating the wavelength of light subject to calibration generated by a light source subject to calibration to a desired wavelength. Elements of optical calibration system 100 that correspond to elements of optical calibration system 10 described above with reference to in FIG. 1 are indicated using the same reference numerals and will not be described again here. The optical calibration system 100 will be described being used to calibration the wavelength of the light subject to calibration 24 generated by light source subject to calibration 32.

The optical calibration system 100 of FIG. 6 is composed of an optical wavelength standard 111 in accordance with the invention and an optical calibration apparatus 152. In the optical wavelength standard 111, the end 26 of the optical fiber 18 of the input optical arrangement 15 is connected to receive sample light from the light source subject to calibration 32, and the end 44 of the optical fiber 43 of the output optical arrangement 17 is connected to deliver the reflected light 14 to the optical calibration apparatus 152.

The input optical arrangement 15 is arranged to illuminate the diffractive surface 21 of the diffraction grating 22 with polarized incident light 13 at a defined angle of incidence α. In this embodiment, incident light 13 with which the input optical arrangement illuminates the diffractive surface is the sample light 31 received from the light source subject to calibration 32. The sample light 31 is a sample of the light subject to calibration 24 generated by the light source subject to calibration 32. Thus, the input optical arrangement 15 can be said to illuminate the diffractive surface 21 of the diffraction grating 22 with the light subject to calibration.

The configuration of the diffractive surface 21 of the diffraction grating 22 and the angle of incidence α are such that the resonance wavelength of the surface plasmons induced at the diffractive surface 21 by the incident light 13 is at the desired reference wavelength of the optical wavelength standard 11. The incident light 13 is absorbed by the surface plasmons induced by the incident light when the wavelength of the incident light is equal to the resonance wavelength. Thus, the surface plasmons induced in the diffraction grating 22 absorb the sample light 31 received as the incident light 13 from the light source subject to calibration 32 when the wavelength of the light subject to calibration is equal to the reference wavelength, and the intensity of the reflected light received by the output optical arrangement 17 is a minimum. When the wavelength of the incident light generated by the light source subject to calibration differs from the resonance wavelength, the incident light 13 does not induce resonance in the surface plasmons of the diffractive surface 21, and absorption of the incident light is substantially less than at the resonance wavelength. In this case, the intensity of the reflected light 14 received by the output optical arrangement is greater than the minimum.

The optical calibration apparatus 152 measures the intensity of the reflected light 14 received from the optical wavelength standard 111 and provides a control signal 163 to the light source subject to calibration 32. The control signal 163 instructs the light source 132 to change the wavelength of the light subject to calibration 24, e.g., to increase or decrease the wavelength of the light 24. The light source 32 changes the wavelength of the light subject to calibration in response to the control signal. As the wavelength of the light subject to calibration approaches the resonance wavelength, the surface plasmons induced in the diffractive surface 21 of the diffraction grating 22 begin to absorb the incident light 13, and the intensity of the reflected light 14 measured by the optical calibration apparatus 152 begins to fall. The measured intensity reaches a minimum when the wavelength of the light subject to calibration is equal to the resonance wavelength. The control signal 163 generated by the optical calibration apparatus 152 then precisely tunes the wavelength of the light source subject to calibration 32 to minimize the intensity of the reflected light 14.

In an embodiment, a small, low-frequency wavelength dither is introduced into the optical calibration system 100 to allow the optical calibration apparatus 152 to operate as part of a phase-locked loop control system that sets the wavelength of the light subject to calibration to a value that minimizes the intensity of the reflected light 14. Such phase-locked loop control systems are known in the art. The dither may be imposed on the wavelength of the light subject to calibration or on the wavelength of the optical wavelength standard 111. The dither may be imposed on the optical wavelength standard by varying the angle of incidence or by varying the pitch of the diffractive surface 21, for example.

Figure 5C:
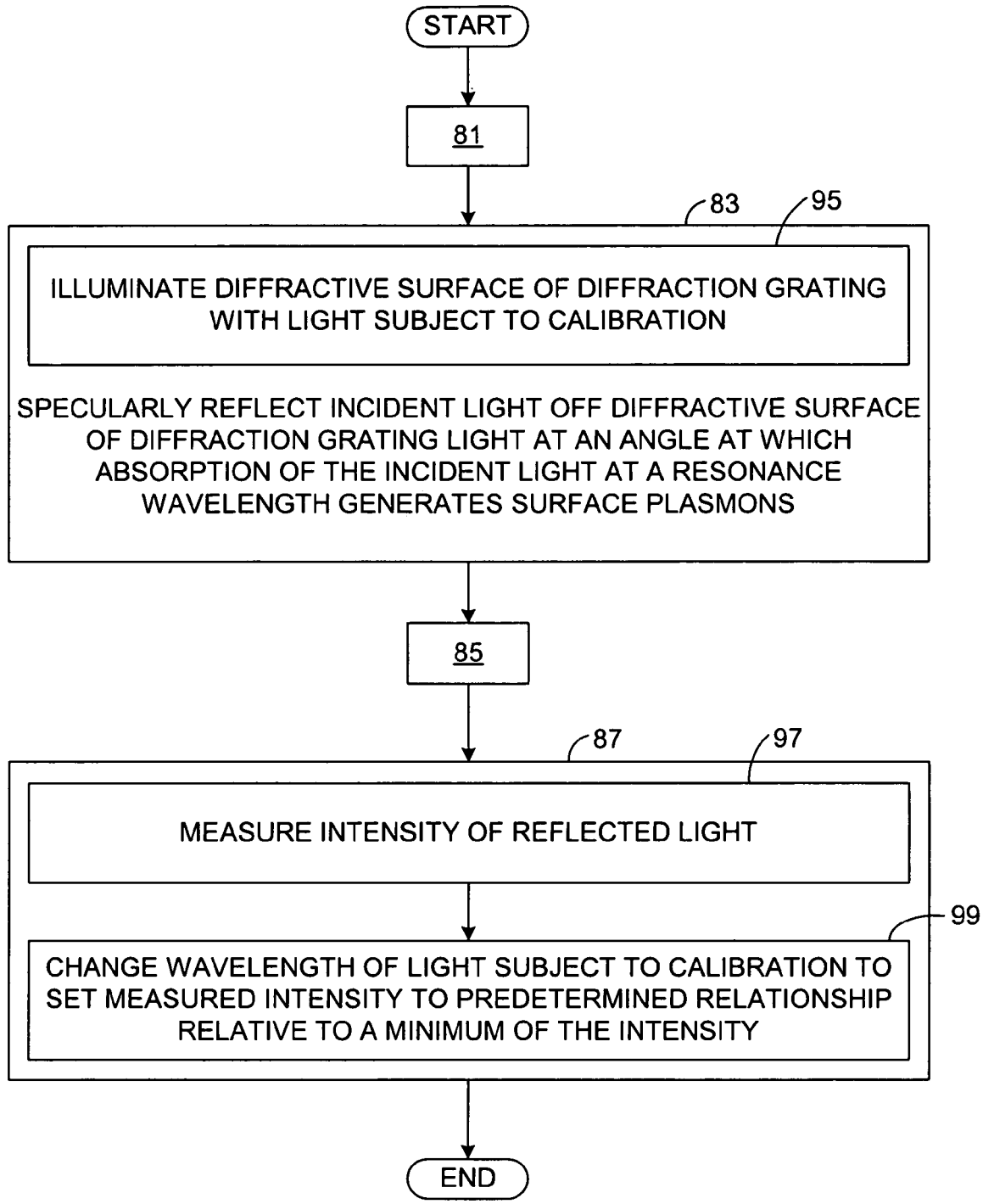
FIG. 5C is a flow chart that illustrates an example of the optical wavelength calibration method shown in FIG. 5A in which the incident light that illuminates the diffractive surface is the light subject to calibration.

FIG. 5C is a flow chart that illustrates an example of the optical wavelength calibration method shown in FIG. 5A in which the incident light that illuminates the diffractive surface is the light subject to calibration. Elements of the method shown in FIG. 5C that correspond to elements of the method shown in FIG. 5A are indicated using the same reference numerals and will not be described again.

The embodiment of block 83 shown in FIG. 5C includes block 95 in which the diffractive surface of the diffraction grating is illuminated with the light subject to calibration as the incident light.

Block 87 in FIG. 5C is composed of blocks 97 and 99. In block 97, the intensity of the reflected light is measured. In block 99, the wavelength of the light subject to calibration is changed to set the measured intensity to a predetermined relationship relative to a minimum of the intensity.

In an example of blocks 97 and 99 performed by the optical calibration system 100 described above with reference to FIG. 6, the predetermined relationship is one of equality, i.e., the wavelength of the light subject to calibration is changed to minimize the measured intensity. The wavelength of the light subject to calibration may be calibrated to a desired wavelength different from the resonance wavelength by calculating the intensity versus wavelength characteristic of the absorption line of the optical wavelength standard. Then, in block 99, the wavelength of the light subject to calibration is changed to set the measured intensity to a value relative to the minimum intensity equal to the calculated intensity difference corresponding to the wavelength difference between the desired wavelength and the resonance wavelength.

This disclosure describes the invention in detail using illustrative embodiments. However, the invention defined by the appended claims is not limited to the precise embodiments described.

We claim:

1. An optical calibration system, comprising:
   a diffraction grating comprising a diffractive surface;
   an input optical arrangement located to illuminate the diffractive surface of the diffraction grating with incident light at an angle of incidence at which absorption of the incident light at a resonance wavelength generates surface plasmons; and
   an output optical arrangement located to receive the incident light specularly reflected by the diffractive surface of the diffraction grating as reflected light, the reflected light including an absorption line at the resonance wavelength;
   a light source; and
   an optical calibration apparatus operable to provide a control signal for calibrating the light source based on the absorption line,
   in which the light source is operable to control a wavelength of light generated by the light source based on the control signal.

2. The optical calibration system of claim 1, in which the diffractive surface comprises metal.

3. The optical calibration system of claim 1, in which:
   the light source is operable to generate the incident light in a range of wavelengths spanning the resonance wavelength; and
   the input optical arrangement comprises an optical fiber arranged to receive the incident light from the light source and to direct the incident light towards the diffractive surface.

4. The optical calibration system of claim 3, in which the input optical arrangement additionally comprises a collimator and a polarizer arranged in series between an end of the optical fiber remote from the light source and the diffractive surface of the diffraction grating.

5. The optical calibration system of claim 1, in which the input optical arrangement comprises an optical fiber, a collimator and a polarizing element arranged in series.

6. The optical calibration system of claim 1, in which the output arrangement comprises a focusing element and an optical fiber arranged in series.

7. The optical calibration system of claim 1, in which the input optical arrangement is connected to receive the light generated by the light source as the incident light.

8. The optical calibration system of claim 1, in which the light source is operable to generate light at the resonance wavelength based on the control signal.

9. The optical calibration system of claim 1, in which the light source is operable to generate the incident light.

10. The optical calibration system of claim 1, in which the light source is operable to generate light subject to calibration and the optical calibration apparatus is operable to compare the light subject to calibration and the incident light specularly reflected by the diffractive surface of the diffraction grating.

11. An optical calibration system for calibrating the wavelength of light subject to calibration generated by a light source subject to calibration at a wavelength determined by a control signal, the system comprising:
   an auxiliary light source operable to generate incident light in a wavelength range spanning a resonance wavelength;
   an optical wavelength standard, comprising:
      a diffraction grating comprising a diffractive surface;
      an input optical arrangement located to illuminate the diffractive surface of the diffraction grating with the incident light at an angle of incidence at which absorption of the incident light at the resonance wavelength generates surface plasmons, the input optical arrangement arranged to receive the incident light from the auxiliary light source; and
      an output optical arrangement located to receive the incident light specularly reflected by the diffractive surface of the diffraction grating as reflected light, the reflected light including an absorption line at the resonance wavelength; and
   an optical calibration apparatus arranged to receive the light subject to calibration and additionally to receive the reflected light from the output optical arrangement, the optical calibration apparatus operable to perform a wavelength comparison between the absorption line in the reflected light and the light subject to calibration and to provide the control signal to the light source subject to calibration, the control signal representing a wavelength difference between absorption line and the light subject to calibration.

12. The optical calibration system of claim 11, in which the optical calibration apparatus is configured to determine a wavelength difference between the absorption peak and the light subject to calibration and to generate the control signal to reduce the wavelength difference to a predetermined difference.

13. The optical calibration system of claim 12, in which the predetermined difference is zero.

14. An optical calibration system for calibrating the wavelength of light subject to calibration generated by a light source subject to calibration at a wavelength controlled by a control signal, the system comprising:
   an optical wavelength standard, comprising:
      a diffraction grating comprising a diffractive surface;
      an input optical arrangement located to illuminate the diffractive surface of the diffraction grating with incident light at an angle of incidence at which absorption of the incident light at a resonance wavelength generates surface plasmons, the input optical arrangement arranged to receive from the light source subject to calibration the light subject to calibration as the incident light; and
      an output optical arrangement located to receive the incident light specularly reflected by the diffractive surface of the diffraction grating as reflected light, the reflected light including an absorption line at the resonance wavelength; and
   an optical calibration apparatus arranged to receive the reflected light from the output optical arrangement, the optical calibration apparatus operable to generate the control signal in response to the intensity of the reflected light and to provide the control signal to the light source subject to calibration.

15. The optical calibration system of claim 14, in which the optical calibration apparatus is configured to generate the control signal to the wavelength of the light subject to calibration to set the intensity of the reflected light to a predetermined relationship to a minimum of the intensity.

16. The optical calibration system of claim 15, in which the predetermined relationship is equality.

17. A calibration method for calibrating the wavelength of light subject to calibration, the method comprising:
   providing a diffraction grating comprising a diffractive surface;
   specularly reflecting incident light off the diffractive surface of the diffraction grating at an angle of incidence at which absorption of the incident light at a resonance wavelength generates surface plasmons;
   receiving the light reflected by the diffractive surface as reflected light, the reflected light having an absorption line at the resonance wavelength; and
   calibrating the wavelength of the light subject to calibration using the absorption line in the reflected light as a wavelength reference, in which the calibrating comprises setting the wavelength of the light subject to calibration.

18. The method of claim 17, in which the calibrating comprises determining a wavelength difference between the absorption line in the reflected light and the light subject to calibration, and in which the setting comprises changing the wavelength of the light subject to calibration in response to the wavelength difference.

19. The method of claim 17, in which the reflecting comprises illuminating the diffractive surface of the diffraction grating with light in a wavelength range spanning the resonance wavelength as the incident light.

20. The method of claim 19, in which the calibrating comprises determining a wavelength difference between the absorption line in the reflected light and the light subject to calibration, and in which the setting is performed in response to the wavelength difference.

21. The method of claim 20, in which the setting comprises changing the wavelength of the light subject to calibration to set the wavelength difference to a predetermined wavelength difference.

22. The method of claim 21, in which the predetermined difference is zero.

23. The method of claim 21, in which the reflecting comprises illuminating the diffractive surface with the light subject to calibration as the incident light.

24. A calibration method, the method comprising:
   providing a diffraction grating comprising a diffractive surface;
   specularly reflecting incident light off the diffractive surface of the diffraction grating at a first angle of incidence at which absorption of the incident light at a first resonance wavelength generates surface plasmons;
   receiving the light reflected by the diffractive surface at the first angle of incidence as first reflected light, the first reflected light having an absorption line at the first resonance wavelength;
   calibrating a wavelength of light subject to calibration using the absorption line in the first reflected light as a wavelength reference;
   specularly reflecting incident light off the diffractive surface of the diffraction grating at a second angle of incidence at which absorption of the incident light at a second resonance wavelength generates surface plasmons;
   receiving the light reflected by the diffractive surface at the second angle of incidence as second reflected light, the second reflected light including an absorption line at the second resonance wavelength; and
   calibrating a wavelength of light subject to calibration using the absorption line in the second reflected light as a wavelength reference.

* * * * *